United States Patent [19]

Bornengo et al.

[11] Patent Number: 4,795,838
[45] Date of Patent: Jan. 3, 1989

[54] PROCESS FOR THE PREPARATION OF (2,2)-PARACYCLOPHANE AND DERIVATIVES THEREOF

[75] Inventors: Giorgio Bornengo, Novara; Alessandro Malacrida, Sovico; Stefano Campolmi, Novara; Maurizio A. Beretta, Milan, all of Italy

[73] Assignee: Montedison S.p.A., Milan, Italy

[21] Appl. No.: 66,507

[22] Filed: Jun. 26, 1987

[30] Foreign Application Priority Data

Jun. 27, 1986 [IT] Italy .................. 20938 A/86

[51] Int. Cl.$^4$ .................. C07C 21/24; C07C 25/18
[52] U.S. Cl. .................. 570/184; 570/183
[58] Field of Search .................. 570/183, 184

[56] References Cited

U.S. PATENT DOCUMENTS

| | | | |
|---|---|---|---|
| 3,221,068 | 11/1965 | Gorham | 570/184 |
| 3,349,142 | 10/1967 | Yeh | 570/183 |
| 4,532,369 | 7/1985 | Hartner | 570/183 |

FOREIGN PATENT DOCUMENTS

| | | | |
|---|---|---|---|
| 704487 | 2/1965 | Canada | 570/129 |
| 807196 | 1/1959 | United Kingdom | 564/282 |

OTHER PUBLICATIONS

Reich et al, "J. Amer. Chem. Soc.", vol. 91(13), Jun. 1969, pp. 3534–3543.
Reich et al, "J. Amer. Chem. Soc.", vol. 91(13), Jun. 1969, pp. 3527–3532.

*Primary Examiner*—Werren B. Lone
*Attorney, Agent, or Firm*—Stevens, Davis, Miller & Mosher

[57] ABSTRACT

Process for the preparation of (2,2)-paracyclophane or derivatives thereof by the Hofmann elimination of p-methylbenzyltrimethylammonium hydroxide or derivatives thereof, in an aqueous solution of an alkali metal hydroxide, wherein said elimination is carried out in the presence of a dialkylether of mono- and poly-ethylene glycols having the formula:

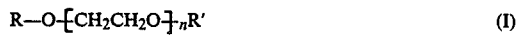

wherein R and R', which may be the same or different, represent alkyl groups having from 1 to 5 carbon atoms, and n is an integer from 1 to 5.

10 Claims, No Drawings

PROCESS FOR THE PREPARATION OF (2,2)-PARACYCLOPHANE AND DERIVATIVES THEREOF

DESCRIPTION OF THE INVENTION

This invention relates to a process for the preparation of (2,2)-paracyclophane and derivatives thereof having the formula:

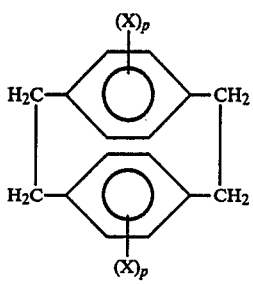

wherein X may be a halogen, an alkyl, an aralkyl, or a halogen-aralkyl radical that may have up to 20 carbon atoms, and p is zero or an integer from 1 to 4.

More particularly, the invention relates to a process for preparing (2,2)-paracyclophane and its derivatives having the formula (II), starting from p-methylbenzyltrimethylammonium hydroxide having the formula:

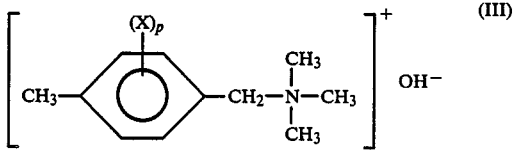

wherein X and p are the same as defined above, by the Hofman elimination.

(2,2)-paracyclophane and its derivatives such as dichloro-(2,2)-paracyclophane, tetrachloro-(2,2)-paracyclophane, tetramethyl-(2,2)-paracyclophane, dimethyl-dichloro-(2,2)-paracyclophane, diethyl-(2,2)-paracyclophane, dibromo-(2,2)-paracyclophane, etc., are products well known in the literature and are generally utilized as intermediates in the preparation of the corresponding poly-p-xylylenes. These polymers, and in particular poly-p-xylylene and its chlorinated derivatives, are advantageously utilized in the form of coating films in the field of the conformal coating obtained by application according to the vacuum vapor deposition technique, in the electronic field.

Various processes have been proposed for preparing (2,2)-paracyclophane (II) and its derivatives. However, such known processes are not fully satisfactory and are not suitable for being adopted on an industrial scale, mainly due to the low productivity of the process and to the difficulty in recovering the product from the reaction mixture.

Thus, for example, *Organic Syntheses*, Collective Vol. 5, John Wiley & Sons, Inc., New York/London, Sydney/Toronto, 1973, pages 883–886, describes a process for preparing (2,2)-paracyclophane by Hofmann elimination starting from p-methylbenzyltrimethylammonium hydroxide obtained by reacting the corresponding bromide with silver oxide. The elimination is carried out in the presence of an alkaline hydroxide and of an inert organic solvent (toluene) and a yield of about 10% is attained.

According to European patent application No. 108,297, it is possible to increase the reaction yield by carrying out the Hofmann elimination in an alkaline medium and in the presence of large amounts of dimethyl sulphoxide. The large volumes and the long reaction times, generally exceeding 50 hours, lead to a low productivity in spite of high yields (about 70%). Furthermore, the recovery of dimethylsulphoxide and the unsatisfactory quality of the resulting product render this process little attractive for industrial-scale utilization.

Generally, in all the known processes for producing (2,2)-paracyclophane, rather large amounts of poly-p-xylylene are formed, which, in the presence of large amounts of organic solvent in the reaction medium, assumes a gelatine-like appearance and is difficult to be filtered off.

According to the present invention, it has now been discovered that (2,2)-paracyclophane and derivatives thereof having formula (II) may be prepared in a pure form, with industrial yields, such as higher than 50% mols, by carrying out the Hofmann elimination of p-methylbenzyltrimethylammonium hydroxide, optionally substituted in the nucleus, of formula (III), in alkaline medium and in the presence of a dialkylether of mono-and poly-ethylene glycols (glyme) having the formula:

$$R-O\text{-}[CH_2CH_2O]_n\text{-}R' \qquad (I)$$

wherein R and R', which may be the same or different, represent alkyl radicals having from 1 to 5 carbon atoms, and n is an integer from 1 to 5.

The p-methylbenzyltrimethylammonium hydroxide of formula (III), optionally substituted in the nucleus, may be prepared starting from the corresponding halide (chloride, bromide) by means of any per se conventional process. In practice, p-methylbenzyltrimethylammonium hydroxide, optionally substituted in the nucleus, is preferably formed in situ by the action of the alkali metal hydroxide present in the reaction medium. As an alternative, said hydroxide of formula (III) may be prepared separately by eluting an aqueous solution of the corresponding halide through a basic ion exchange resin column.

Examples of di-alkyl ethers of mono- and poly-ethylene glycols having formula (I) which may be utilized in the process of the present invention are: di-ethylene-glycol-di-methyl ether, tetraethylene-glycol-di-methyl ether, di-ethylene-glycol-di-ethyl ether, di-ethylene-glycol-methyl-ethyl ether, penta-ethylene-glycol-di-methyl-ether, di-ethylene-glycol-di-propyl ether, etc.

The amount of di-alkyl ether of mono- and poly-ethylene-glycols or mixtures thereof of formula (I) to be added in the reaction medium may vary over a wide range. Thus, weight ratios of di-alkyl ether of formula (I)/p-methylbenzyl trimethyl ammonium hydroxide of formula (III) of between 2 and 50, and preferably between 4 and 10, may be used.

According to this invention, the Hofmann elimination is carried out in an alkaline medium consisting or consisting essentially of an aqueous solution of an alkali metal hydroxide having a concentration higher than 10% by weight. An alkali metal hydroxide, sodium or potassium hydroxide may be used. The aqueous solution is preferably maintained during the Hofman elimination reactin at a concentration between 15 and 35% by weight.

Molar ratios of the alkali metal hydroxide to the p-methylbenzyltrimethylammonium hydroxide (III) between 1 and 10 are advantageously used.

The Hofmann elimination reaction is carried out at a temperature between 50° and 150° C., preferably between 70° and 120° C., and for a time of 1 to 40 hours, and preferably for 5 to 20 hours, in an aqueous solution of alkali metal hydroxide.

Inert organic solvents which are not miscible with water may be added to the reaction medium. Particularly suitable for use as the inert organic solvents are: toluene, xylene, benzene, tetraline, etc.

At the end of the Hofmann elimination reaction, the resulting product is separated according to per se known and substantially conventional methods.

The process of this invention permits one to obtain, with industrially acceptable yields generally higher than 50% by moles and in a few cases even higher than 70% by mols, (2,2)-paracyclophane and its derivatives substituted in the nucleus, with a high degree or purity (above 98%) and a high productivity.

The present invention is still further elucidated by the following examples, which however are to be construed as merely illustrative. In the examples, unless otherwise specified, all parts, percentages, and ratios are by weight.

EXAMPLE 1 (COMPARATIVE TEST)

Into a 1,000 ml flask equipped with a stirrer, thermometer, and condenser, there were charged:

60 g of an aqueous solution containing 40% by weight of NaOH (0.6 moles); and 62.5 g of an aqueous solution containing 63.9% by weight of p-methylbenzyltrimethylammonium chloride (0.2 moles).

Under continuous stirring, the resulting solution was gradually heated to a temperature of 120° C. The sodium hydroxide concentration was maintained at 30% by weight. The solution was maintained at the boiling temperature over the course of 5 hours.

The resulting (2,2)-paracyclophane was separated from the reaction mass by solubilization in 300 ml of xylene. For this purpose, xylene was added to the reaction mass and the slurry was maintained at full reflux under stirring during 0.5 hour. The reaction mass was filtered at 95° C., the aqueous phase was separated from the organic solution, and this solution was repeatedly washed with water and concentrated to a small volume. The xylene solution was cooled down to 20° C. and the precipitated solid was recovered by filtration. After washing the solid with acetone and drying, there were obtained 1.08 g of a crystalline white solid (yield 5.2% by moles), having a melting point of 283° to 285° C., which, on gas-chromatographic analysis, proved to be (2,2(2,2) -paracyclophane having a degree of purity of about 99.5%.

EXAMPLE 2

Into a 500 ml flask equipped with a thermometer, stirrer, condenser, and valves for $N_2$ flow, there were charged:

19.95 g of p-methylbenzyltrimethylammonium chloride (0.1 moles);
90 g of $H_2O$;
24 g of NaOH (0.6 moles); and
115 g of tetraethylene glycol dimethyl ether (tetragly(tetraglyme).

Under continuous stirring and in a stream of $N_2$, the solution solution was gradually heated bringing the temperature up to 90° C.

The reaction mixture was maintained under these conditions over the course of 10 hours.

The cooled raw material was diluted with 300 g of $H_2O$ and the sand the solid mass thus obtained was filtered.

The pecipitate was treated with 250 g xylene for 0.5 hours.

The reaction mass was filtered at 95° C. and the organic phase wasphase was concentrated to a low volume.

The xylene solution was cooled at 20° C. and the precipitated solid product was recovered by filtration.

After washing the solid product with acetone and after drying, there were thus obtained 7.3 g of a white crystalline solid product (yield 70% by moles) having a melting point of 283° to 285° C. and proving by gas-chromatographic analysis to be (2,2)-paracyclophane paracyclophane with a purity of about 99.5%.

EXAMPLE 3

Into a 500 ml flask equipped with a stirrer, thermometer, condenser, and valves for the flow of $N_2$ there were charged:

23.4 g of p-methyl benzyl ammonium chloride monochloro-substituted in the nucleus (0.1 moles);
96 g of $H_2O$;
38g of KOH at 85% (0.575 moles);
115 g of diethylene-glycol-di-methyl ether (diglyme).

Under continuous stirring, and in a stream of $N_2$, the solution was gradually heated bringing the temperature up to 95° C.

The reaction mixture was maintained under these conditions over the course of 10 hours.

A further 6.6 g of KOH at 85% (0.1 moles) were then added and the reaction was completed over a further 2 hours.

The cooled raw material was diluted with 300 g of $H_2O$ and the solid mass thus obtained was filtered.

The precipitate was treated with 250 g of n-hexane, under reflux, for 0.5 hours.

The reaction mass was filtered and from the hexane solution there were obtained, after removal of the solvent, 10.4 g (yield 75% by moles) of a mixture of isomers of dicloro-substituted (2,2)-paracyclophane of the formula:

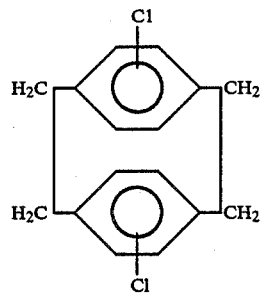

determined to be such by NMR analysis.

The purity of the dichloro-substituted (2,2)-paracyclophane, measured by gas-chromatography, was higher than 98%.

What is claimed is:

1. A process for preparing (2,2)-paracyclophane and derivatives thereof of the formula:

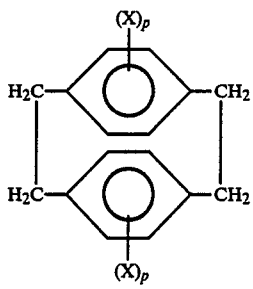 (II)

wherein X is a halogen atom, an alkyl radical, an aralkyl radical, or a halo-aralkyl radical having up to 20 carbon atoms, and p is zero or an integer from 1 to 4, by the Hofmann elimination of p-methylbenzyl trimethylammonium hydroxide or derivatives thereof of the formula:

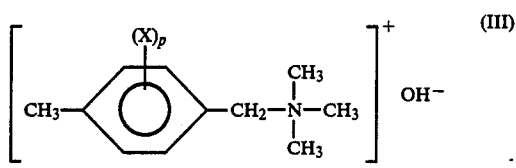 (III)

wherein X and p are the same as defined above, in an aqueous solution of an alkali metal hydroxide, characterized in that said Hofmann elimination is carried out in the presence of at least one di-alkylether of mono- and poly-ethylene glycols having the formula:

R—O—[CH₂CH₂O]ₙR'  (I)

wherein R and R', which may be the same or different, represent alkyl radicals having from 1 to 5 carbon atoms, and n is an integer from 1 to 5.

2. The process according to claim 1, in which the p-methylbenzyltrimethylammonium hydroxide of formula (III) is prepared in situ from the corresponding halide by the action of the alkali metal hydroxide present in the reaction medium.

3. The process according to claim 1, in which the ether of formula (I) is the di-ethylene-glycol-dimethyl ether or the tetra-ethylene-glycol-di-methyl ether.

4. The process according to claim 1, in which the weight ratios: ether of formula (I)/p-methyl-benzyl-trimethyl-ammonium hydroxide of formula (III) is between 2 and 50.

5. The process according to claim 4, in which the weight ratios: ether of formula (I)/p-methyl benzyl-trimethyl ammonium hydroxide of formula (III) is between 4 and 10.

6. The process according to claim 1, in which the concentration of the aqueous solution of the alkali metal hydroxide is maintained, during the Hofmann elimination, between 15 and 35% by weight.

7. The process according to claim 1, in which the molar ratio of the alkali metal hydroxide to p-methyl-benzyl trimethyl ammonium hydroxide of formula (III) is between 1 and 10.

8. The process according to claim 1, in which the Hofmann elimination is carried out at a temperature between 50° and 150° C. and for a time of 1 to 40 hours.

9. The process according to claim 8, in which the Hofmann elimination is carried out at a temperature between 70° and 125° C., and for a time between 2 and 10 hours.

10. The process according to claim 1, in which the Hofmann elimination is carried out in the presence of an inert organic solvent that is not miscible with water.

* * * * *